(12) United States Patent
Kim et al.

(10) Patent No.: US 7,493,703 B2
(45) Date of Patent: Feb. 24, 2009

(54) SURGICAL DEPTH INSTRUMENT

(75) Inventors: John Y. S. Kim, Chicago, IL (US); Young J. Son, Deerfield, IL (US)

(73) Assignee: Eidosmed LLC, Chicago, IL (US)

( * ) Notice: Subject to any disclaimer, the term of this patent is extended or adjusted under 35 U.S.C. 154(b) by 167 days.

(21) Appl. No.: 11/376,399

(22) Filed: Mar. 15, 2006

(65) Prior Publication Data

US 2006/0207119 A1    Sep. 21, 2006

Related U.S. Application Data

(63) Continuation-in-part of application No. 11/081,147, filed on Mar. 16, 2005, now Pat. No. 7,165,336.

(51) Int. Cl.
*A61B 5/107* (2006.01)

(52) U.S. Cl. ......................................... 33/512

(58) Field of Classification Search ............. 33/512
See application file for complete search history.

(56) References Cited

U.S. PATENT DOCUMENTS

| | | | |
|---|---|---|---|
| 1,526,418 | A | 2/1925 | Gronner |
| 3,916,529 | A | 11/1975 | Mousseau |
| 3,943,914 | A | 3/1976 | Grenfell et al. |
| 4,005,527 | A | 2/1977 | Wilson et al. |
| 4,033,043 | A | 7/1977 | Cunningham |
| 4,432,376 | A | 2/1984 | Huszar |
| 4,708,647 | A | 11/1987 | Pippin et al. |
| 4,845,646 | A | 7/1989 | Marquis et al. |
| 5,013,318 | A | 5/1991 | Spranza, III |
| 5,212,871 | A | 5/1993 | Luccarelli |
| 5,801,762 | A | 9/1998 | Dianna et al. |
| 6,145,509 | A | 11/2000 | Tanner |
| 6,494,848 | B1 | 12/2002 | Sommercorn et al. |
| 6,665,948 | B1 | 12/2003 | Kozin et al. |
| 7,165,336 | B2 * | 1/2007 | Kim ............................ 33/512 |
| 2003/0047009 | A1 | 3/2003 | Webb |
| 2006/0041241 | A1 | 2/2006 | Herndon |

FOREIGN PATENT DOCUMENTS

| | | |
|---|---|---|
| WO | WO 00/78258 A1 | 12/2000 |
| WO | WO 2005/027745 A1 | 3/2005 |

* cited by examiner

*Primary Examiner*—Christopher W Fulton
(74) *Attorney, Agent, or Firm*—Drinker Biddle & Reath LLP (57) ABSTRACT

An instrument for measuring the depth of a hole in a bone or other tissue electronically, and for providing a convenient display of information relating to the depth. The surgical depth gauge comprises a probe insertable into the hole with an indented hook for positioning the distal end of the probe against a distal surface of the bone, and a reciprocating member slidably connected to the probe and positionable against a proximal surface of the bone. The probe cooperates with a sensor in an electronic circuit connected to the reciprocating member to produce an electronic signal that changes with the distance between the first surface and the second surface. The electronic circuit comprises a power source and a display. The instrument is robust to contamination and sterilization, and is designed for use by both left and right-handed surgeons.

38 Claims, 5 Drawing Sheets

FIG. 1

FIG. 3

SURGICAL DEPTH INSTRUMENT

CROSS REFERENCE TO RELATED APPLICATIONS

This application is a continuation-in-part of U.S. patent application Ser. No. 11/081,147, filed on Mar. 16, 2005, which issued on Jan. 23, 2007 as U.S. Pat. No. 7,165,336, the entire content of which is incorporated herein by reference.

FIELD OF THE INVENTION

The invention relates to an instrument for determining the depth of a hole and, in particular, a depth gauge for providing a digital measurement of the depth of a hole in a bone.

BACKGROUND OF THE INVENTION

Many surgical procedures require surgeons to secure a device to the bone of a patient. In some procedures, the surgeon spans and secures one or more bones, or pieces of bone, using a bone plate and screws or other fasteners. In other procedures, the surgeon uses a screw or other fastener without another device, for example, to secure a transplanted tendon. In many procedures, the surgeon drills a hole in the bone prior to securing the fastener to the bone. With a hole in place, the surgeon can more easily select a fastener of the appropriate length. Selecting a fastener of appropriate length can be very important. If the fastener is too long, the fastener may protrude from the bone. Typically, the bone abuts against soft tissues that may be harmed if the fastener is too long. Although over-drilling through a metacarpal may result only in minor damage to the fat layer within the finger, if the fastener used after drilling is too long, the patient may experience more serious complications. For example, a fastener that protrudes may be tactilely felt by the patient, prevent soft tissues (such as tendons, ligaments, or muscles) from moving over the bone surface, or even pierce the skin. As a different example, complications such as paralysis may result from a fastener mounted in the pedicle portion of the human spine that protrudes to a point where the fastener contacts the spinal cord.

During drilling, the surgeon is typically capable of feeling when the drill has penetrated through the bone from a drop in resistance of the drill against the bone. Because the simple act of drilling does not provide an exact measurement of the depth of the bone, surgeons sometimes use an analog depth gauge to measure the depth of the hole.

Analog depth gauges typically comprise a central probe member having a barb at the distal end, and a reciprocating sleeve that encircles the proximal end of the central probe member. To measure the depth of a hole in a bone, the surgeon abuts the sleeve against the proximal side of the hole, and extends the probe member into the hole. After extending the probe member beyond the distal side of the hole, the surgeon retracts the probe member, attempting to find purchase against the distal side of the hole with the barb. Typically, a marker is secured to the central probe member and the reciprocating sleeve has a graduated scale (in inches or millimeters) along a portion of its length. The surgeon reads the measurement of depth by examining the position along the graduated scale indicated by the marker secured to the central probe member.

A number of problems are associated with the analog depth gauge. Components of the analog depth gauge are typically manufactured from surgical-grade stainless steel, with the graduated scale embossed along a portion of the length of the reciprocating member, producing a highly reflective surface. Under bright operating room lights, surgeons find it difficult to see the graduated scale of millimeter-wide length increments. An accurate measurement of depth using an analog depth gauge requires the surgeon to make a close examination of the graduated scale while holding the analog depth gauge steady. If the barb loses its purchase on the distal side of the hole, either the accuracy of the measurement is decreased or the time required for surgery must be extended to permit repositioning of the barb. In surgical procedures that require many depth measurements, these difficulties are multiplied.

There are other problems associated with the analog depth gauge. An accurate reading of the graduated scale requires the eyes of the surgeon to be properly aligned with the graduated scale. Viewed from an angle, the position of the marker relative to the graduated scale may be distorted. The eyes of the surgeon may not be properly aligned with the graduated scale while the surgeon is standing erect. The surgeon may have to bend over while using the analog depth gauge to make an accurate reading because if the depth gauge is tilted in order to make the reading, the sleeve will shift relative to the probe, making the measurement less accurate and possibly causing the barb to lose its purchase on the distal side of the hole, resulting in the same disadvantages mentioned above.

Accordingly, there has been a need for an improved depth gauge for surgical procedures.

SUMMARY OF THE INVENTION

The present invention provides a system and a method for faster and more accurate measurements of depth during surgery. In an embodiment, the system of the present invention comprises a probe insertable into a hole in a bone with an indented hook for positioning the distal end of the probe against a first surface of the bone, and a reciprocating member slidably connected to the probe and positionable against a second surface of the bone. A sensor generates an electronic signal that varies with the distance between the first surface and the second surface. In various embodiments, the sensor comprises capacitors, inductors, or both.

The present invention provides the first electronic instrument for depth measurement designed for use in a surgical environment. Surgical instruments are sterilized to prevent infection, typically by exposure to hydrogen peroxide gas. In addition, surgical instruments need to operate consistently, even after exposure to contaminants such as water, blood, or hard and soft tissue. The demands of the surgical environment have thus far posed an obstacle to the design of an electronic depth measuring instrument. Various embodiments of the present invention provide an electronic surgical depth gauge that is robust to sterilization conditions and resistant to contamination. Various embodiments of the present invention also provide a surgical depth instrument that is easy to handle and read, producing consistently accurate measurements of depth.

A variety of electronic sensors or transducers may be employed in practicing the present invention. In some embodiments, the present invention employs inductive elements because of their more robust characteristics in environments with solid or fluid contaminants or sterilization fluids. Inductive elements may be employed in the form of patterned conductive loops used in conjunction with a read head assembly of transmission and receiving loops. As will be understood by one of skill in the art, other sensor arrangements, preexisting or which may be developed in the future, may be used with the present invention, as long as they provide a signal which accurately represents the distance between the distal end of a hook disposed on the end of the probe and a reference surface, such as the end of a tissue guard, of the instrument.

The present invention also comprises a method for using an electronic instrument for depth measurement. In particular, the present invention provides the first method for taking a measurement of depth of a passageway in bone and displaying the measurement digitally. The method of the present invention provides for substantially improved accuracy in surgical measurements of depth, which in turn means fewer problems for surgical patients.

BRIEF DESCRIPTION OF THE DRAWINGS

The foregoing and other objects, advantages, and features of the present invention will be apparent from the following detailed description and the accompanying drawings, in which:

FIG. 2A' shows an enlarged detail of a circled portion of the cross-section shown in FIG. 2A;

FIG. 2B' shows an enlarged detail of a circled portion of the cross-section shown in FIG. 2B;

DETAILED DESCRIPTION OF THE INVENTION

After drilling a hole in a bone during surgery, a surgeon will often use an instrument to measure the depth of the hole before selecting a fastener. The system and method of the present invention are performed using a surgical depth gauge with an electronic sensor and digital display, which provide an easier, faster, and more accurate means for measuring depth during surgery. While a variety of embodiments of the invention are shown in the attached figures, those skilled in the art will recognize that there are other mechanical and electrical arrangements for accomplishing surgical depth measurements digitally in accordance with the present invention. Various alternative embodiments, features and variations are therefore also described herein.

Instruments used for surgical procedures must be robust both to the solid and liquid contaminants encountered during surgery (such as tissue and blood) and the temperatures, pressures, and fluids encountered during sterilization (such as hydrogen peroxide gas). The two embodiments of the present invention shown in the attached drawings illustrate two alternative form factors for the sterilization-proof and contamination-proof surgical depth gauge in accordance with the present invention. In a first embodiment 100 shown in FIGS. 1 through 5, the surgical depth gauge comprises a tissue guard 120, sealed housing 130, and body 140 that are robust to contamination. In addition, the first embodiment 100 can be quickly disassembled and reassembled for sterilization. In a second embodiment 200 shown in FIG. 7, the surgical depth gauge comprises a fully integrated body 235, in which is sealed an electronic sensor and displays. The second embodiment is robust to repeated contamination and sterilization without disassembly.

Figure 1:
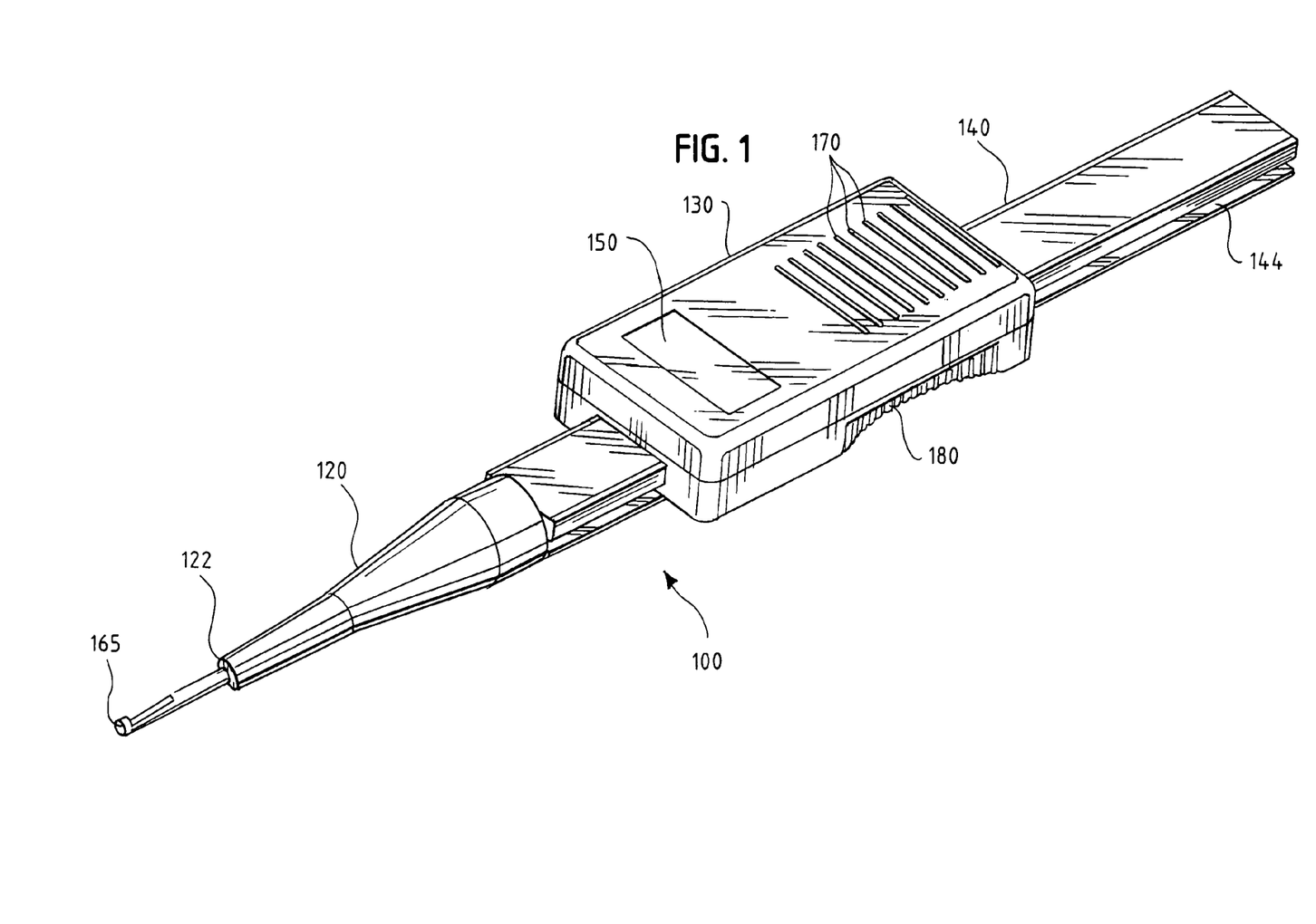
FIG. 1 shows a perspective view from above of a surgical depth instrument in accordance with an embodiment of the present invention.

With a hole already drilled, a surgeon might reach for a surgical depth instrument of the present invention as shown by the instrument 100 of FIG. 1. The instrument 100 comprises a probe 160 with an indented hook 165, and a tissue guard 120 secured to a body 140. A sealed housing 130 slidably engages with a side groove 144 of the body 140 of the instrument 100. As shown in FIG. 1, the sealed housing 130 comprises a display window 150, ergonomic top ridges 170, and ergonomic side grooves with ridges 180. The present invention is adapted for use by either a left-handed or a right-handed surgeon. The side grooves with ridges 180 are concave to the side surface of the sealed housing 130, and are symmetrically disposed on either side of the sealed housing 130.

Figure 7:
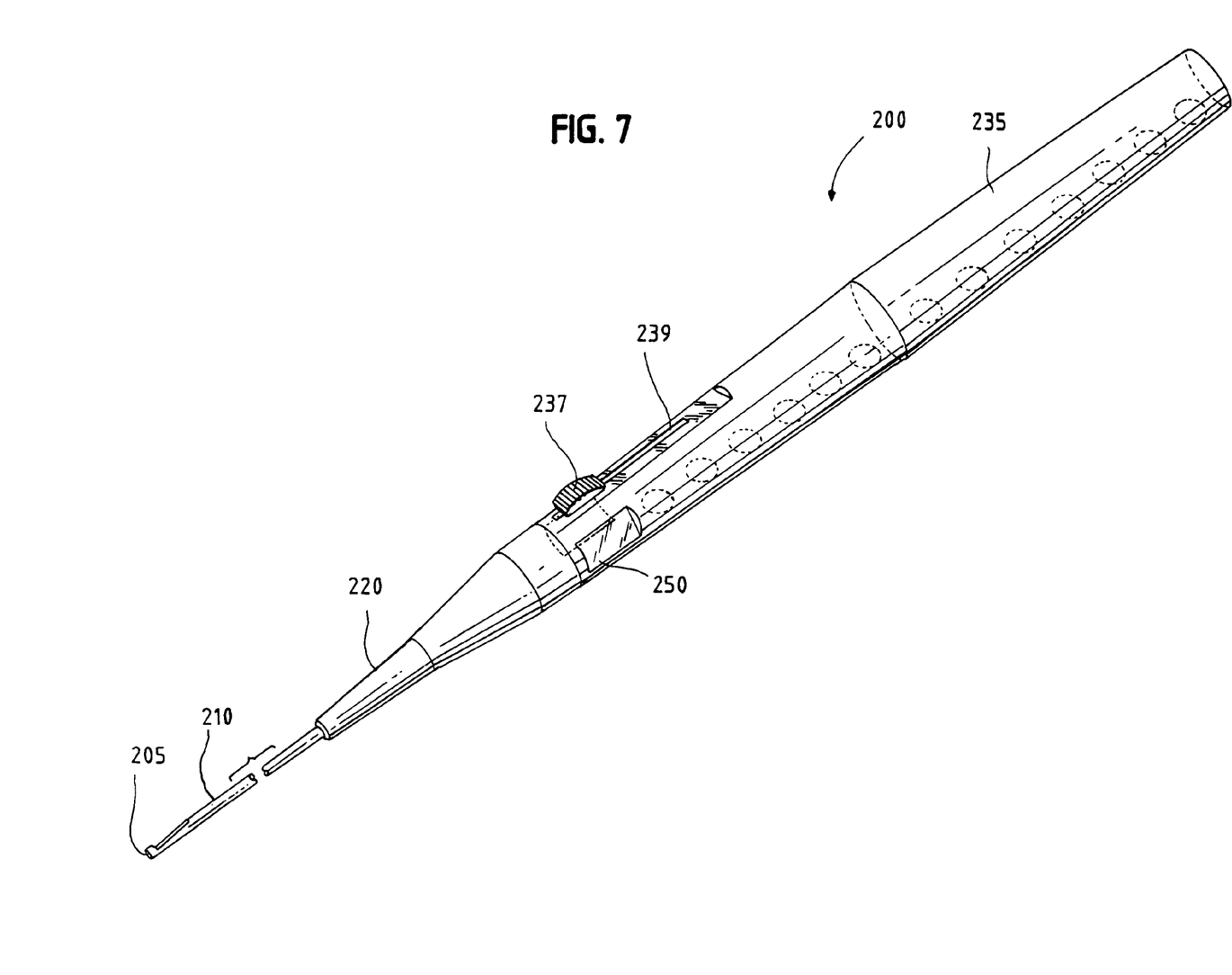
FIG. 7 shows a surgical depth instrument in accordance with a second embodiment of the present invention.

An alternative embodiment of the form factor for the present invention is shown in FIG. 7 as the second embodiment 200. In this alternative embodiment, the invention comprises a substantially cylindrical form factor. As discussed above, the second embodiment 200 comprises an integrated body 235 that is robust to contamination and sterilization without disassembly. Referring to FIG. 7, the second embodiment 200 comprises an integrated body 235 with slide groove 239 and display window 250 formed therein. In accordance with an embodiment, so that the same instrument may be used by both right-handed and left-handed surgeons, a display window 250 (and accompanying display) will be provided on both the right and left sides of the instrument. In other words, with respect to FIG. 7, another display window 250 (and display) will be similarly disposed on the other side of the instrument. The distal end of the integrated body 235 includes a tissue guard 220. In an embodiment, the method of the present invention is practiced by positioning the distal end of the tissue guard 220 against the proximal surface of the bone (as shown in connection with FIGS. 2A and 2B, described below). According to an embodiment, the integrated body 235 of the instrument 200 may be fabricated from two substantially symmetrical pieces that may be disassembled and reassembled to facilitate sterilization. As shown in FIG. 7, the two pieces fit together along a line through the middle of the integrated body 235. In various embodiments, the two pieces may be threaded together, or sealed together by an adhesive resistant to contamination and sterilization. In addition, as shown in FIG. 7, the second embodiment form factor 200 also comprises finger grooves disposed towards its bottom side.

Figure 3:
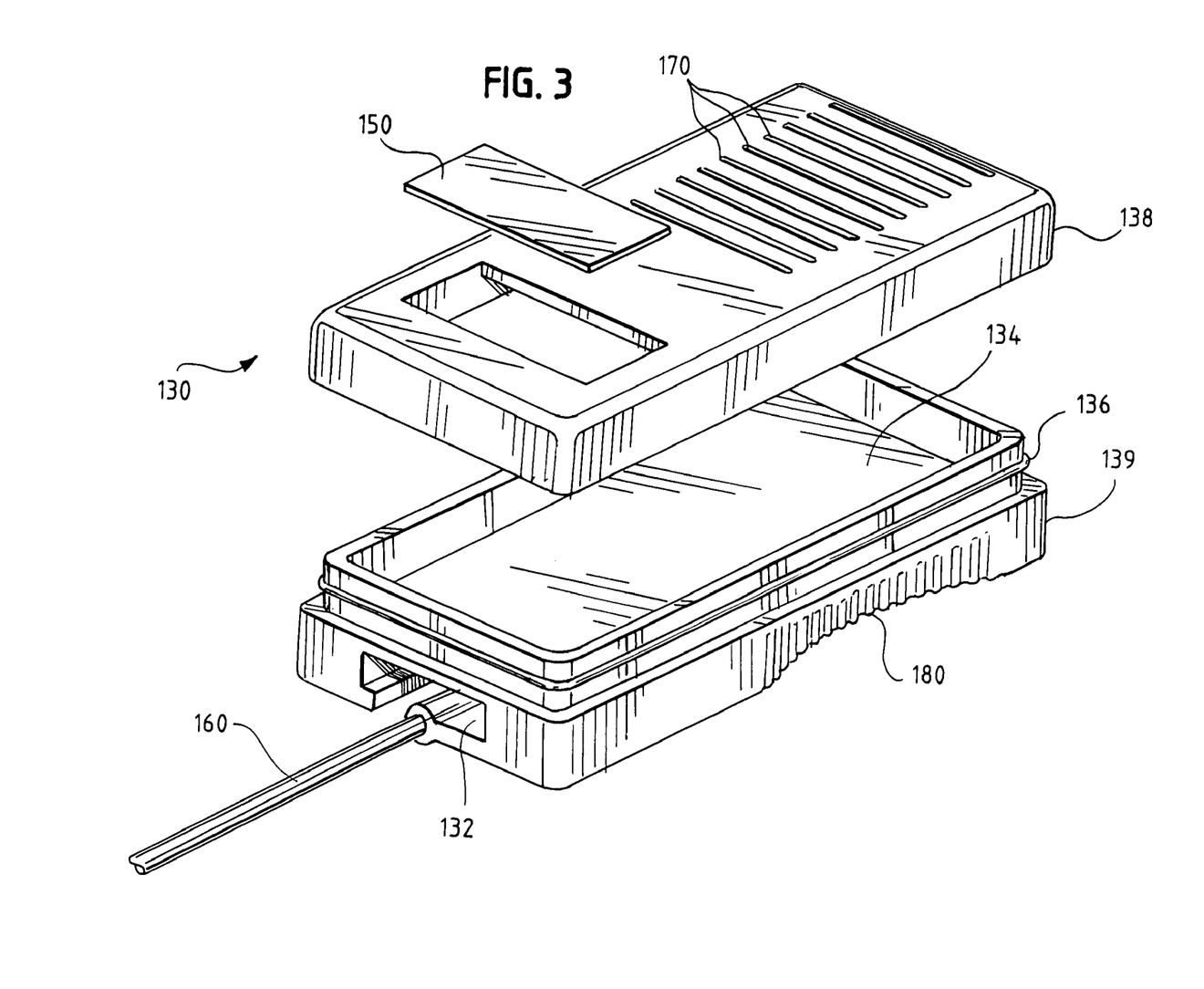
FIG. 3 shows an exploded perspective view of a sealed housing in accordance with an embodiment of the surgical depth instrument of the present invention.

Turning back to the first embodiment of the form factor shown by instrument 100 in FIG. 1, the instrument 100 includes side grooves 180, which are formed in the bottom piece 139 of the sealed housing 130 (see FIG. 3). In other embodiments, however, the side grooves 180 may be formed in both the top piece 138 and bottom piece 139, such that the side grooves extend from top to bottom symmetrically along the sides of the sealed housing 130. As will be appreciated by those of skill in the art, in still other embodiments, the side grooves 180 may be convex to the side surface of the sealed housing 130, and may be formed with a surface of bumps rather than ridges, or with other surfaces that provide friction and a tactile surface, even after exposure to solid or liquid contamination. In addition, in all of the embodiments shown in the attached drawings, the display window 150 is positioned nearer the distal end of the instrument. As will be appreciated by those of skill in the art, the display window 150 may be positioned elsewhere on the instrument, for example, nearer the proximal end. In addition, multiple display windows may be disposed at various locations on the instrument. All such features and variations are contemplated within the scope of the present invention.

Figure 2A:
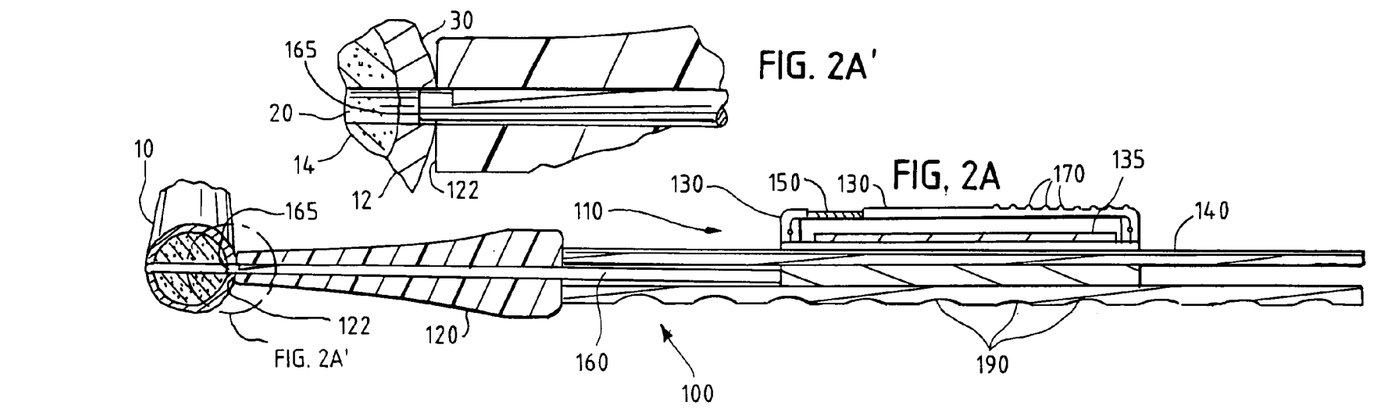
FIG. 2A shows a cross-section of a surgical depth instrument in a retracted position in accordance with an embodiment of the present invention.

An embodiment of the method for taking depth measurements in accordance with the present invention begins with the surgeon holding the instrument 100 in either a right or a left hand. FIG. 2A shows a longitudinal cross-section of the instrument 100 with the probe 160 in a retracted position, and a bone portion 10 shown also in cross-section. In accordance with an embodiment of the method of the present invention, the surgeon begins a depth measurement by locating the position of the hole in the bone portion 10. As shown in the enlarged detail of FIG. 2A', the tip of the indented hook 165 protrudes slightly beyond the distal end 122 of the tissue guard 120, thereby permitting the surgeon to sense the position of the hole when the tip of the indented hook 165 slips into the hole. In this position, the distal end 122 of the tissue guard 120 abuts against the proximal surface 30 of the bone portion 10. In an embodiment, the instrument 100 is calibrated to read zero depth when the catch (or the proximal end) of the hook 165 is flush with the distal end 122 of the tissue guard 120.

Figure 2B:
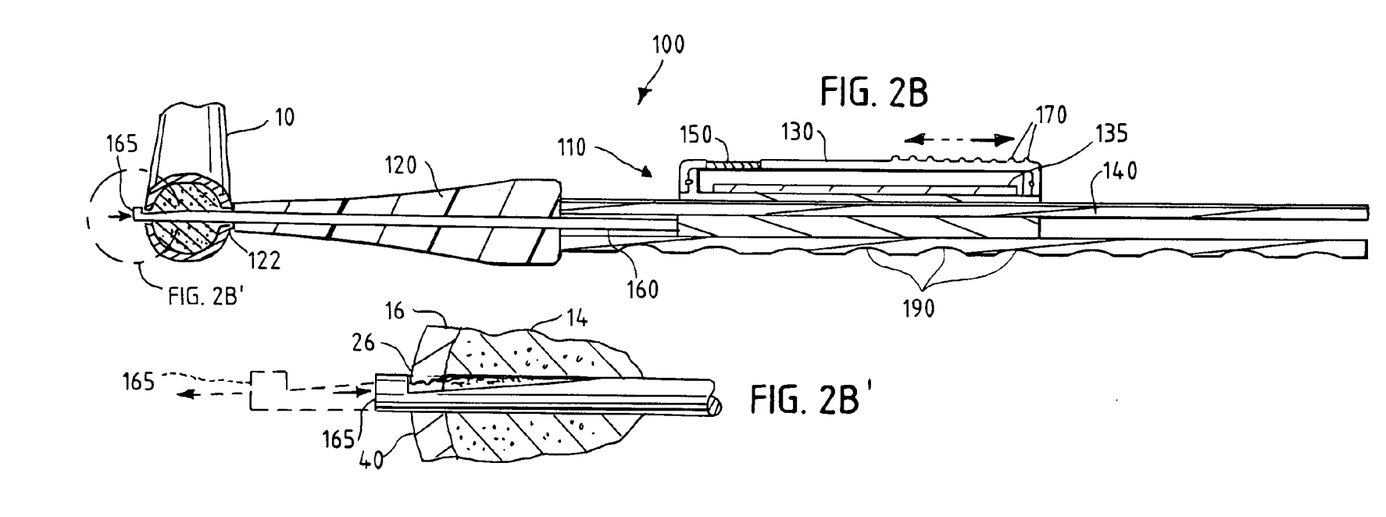
FIG. 2B shows a cross-section of a surgical depth instrument in an extended position and engaged with the distal surface of a bone portion in accordance with an embodiment of the present invention.

In an embodiment, the method of the present invention also comprises a step wherein the surgeon extends the probe 160 into the hole 20 of the bone portion 10. FIG. 2B shows a cross-section of the instrument 100 in an extended position. FIG. 2B' shows an enlarged detail of FIG. 2B, in which the indented hook 165 has purchase on the distal surface 40 of the hole 20. In the cross-sections shown in FIGS. 2B and 2B', the distal end 122 of the tissue guard 120 remains against the proximal surface 30 of the bone portion 10 in which a hole 20 is present. From the position shown in FIG. 2B', the surgeon reads a measurement of depth from an electronic display behind the display window 150 in the compartment 134 of the sealed housing 130.

As shown in FIGS. 2A' and 2B', the bone portion 10 is bicortical, i.e., the bone portion 10 has a first, proximal cortical layer 12 (see FIG. 2A'), a cancellous layer 14, and a second, distal cortical layer 16 (see FIG. 2B'). It should be noted, however, that the present invention is suitable for use with bones having other structures, including solid cortical, unicortical, or cancellous bones. The present invention may even be used for surgical depth measurement of holes or cavities in other types of tissue.

As described above, the hole 20 may be a hole formed in the bone portion 10. In using the instrument 100 to measure the distance from a proximal surface 30 formed on the proximal cortical layer 12 to a distal surface 40 formed on the distal cortical layer 16, the instrument 100 operates so that the distance between the distal end 122 of the tissue guard 120 (which abuts the proximal surface 12) and the proximal end of the indented hook 165 (which has purchase on the distal surface 16) is determined by an electronic sensor, generating a precise measurement of the distance between the proximal surface 30 and distal surface 40. The electronic sensor may comprise inductive or capacitive elements in a read assembly on a printed circuit board and inductive or capacitive elements in an increment assembly on a printed circuit board within the compartment 146 of the body 140 (see FIG. 5). More specifically, the probe 160 of the instrument 100 is inserted into the proximal edge 22 of the hole 20, through the hole 20, and out from a distal edge 26 of the hole 20, such that the indented hook 165 of the probe 160 extends beyond the distal surface 40 of the bone portion 10. Extension of the indented hook 165 away from the body 140 is accomplished in accordance with the instrument 100 by pressing a thumb or forefinger against the top ridges 170 on the sealed housing 130. As should be clear to those of ordinary skill in the art, if the hole 20 is a hole formed by a drill bit of cylindrical symmetry, the proximal and distal edges 22 and 26 will be approximately circular.

The distal end of the probe 160 is equipped with an indented hook 165 in the instrument 100 shown in FIGS. 1, 2, 4 and 7. In other embodiments, however, the indented hook 165 may be replaced with another means for detecting the distal surface 40. In particular, FIGS. 6A and 6B show in profile alternative mechanical embodiments of the distal end of the probe 160. FIG. 6A shows a barb 167 at the distal end of the probe 160. FIG. 6B shows a hook 169 at the distal end of the probe 160.

With the indented hook 165 at its distal end, the probe 160 can take purchase on the distal surface 40 of the bone portion 10. The instrument 100 is shown in this position in FIGS. 2B and 2B'. Once the indented hook 165 has completely passed through the distal edge 26, the shaft of the probe 160 is shifted slightly, laterally so that the indentation in the indented hook 165 abuts against the distal edge 26. A slight retraction of the probe 160 then permits the indented hook 165 to engage (or take purchase on) the distal surface 40 of the distal cortical layer 16. Retraction of the indented hook 165 is accomplished in accordance with the instrument 100 by squeezing the side grooves 180 with thumb and forefinger, and pulling lightly. In this manner, the proximal surface of the indented hook 165 and the distal end of the tissue guard 120, respectively, are positioned against the distal surface 40 and proximal surface 30 of the bone portion 10 and, through the use of slight tension, are retained thereon. In reading the electronic display when the invention is maintained in this physical configuration, the surgeon is provided with an accurate measurement of the depth of the hole 20 in the bone portion 10.

Although in the embodiment depicted in FIG. 1, the probe 160 includes a mechanical securement (in the form of an indented hook 165), other mechanical and nonmechanical means for positioning the distal end of the probe 160 against the distal surface 40 of the bone portion 10 may be used in other embodiments of the present invention. In particular, electronic sensors may be used in other embodiments to detect where the distal surface 40 terminates. For example, an ultrasonic transducer, optical or other sensor may be used to detect where the distal surface 40 terminates by measuring differential acoustic or optical reflectivity or transmissivity or other characteristics as the probe 160 traverses the hole 20. In such embodiments, an electronic sensor may be mounted to the distal end of the probe 160 in a configuration perpendicular to the length of the probe 160. Alternatively, the distal end of the probe 160 may include only a perforation disposed perpendicular to the length of the probe 160, and a conduit that provides an acoustical, optical, or electrical connection to a sensor included in the sealed housing 130. As will be recognized by skilled artisans, such a conduit might be provided by a hollow probe, fiber optic, or insulated wire, respectively. Moreover, in some embodiments, a current-sensing device may be placed in electrical connection (for example, with an insulated wire) with the distal end of the sensor to detect a change in the resistivity or conductivity of the environment local to the distal end of the probe 160.

The instrument 100 further includes a reference portion that abuts the proximal surface 30. In the embodiment of the invention shown in the attached drawings, the reference portion is provided by a tissue guard 120. The tissue guard 120, as shown by way of example in FIGS. 1, 2, 4 and 7, has a tapered conical shape. The tissue guard includes a cylindrical hollow at its core, through which the probe 160 may extend and retract. In other embodiments, the tissue guard may take a narrower, longer, or more elongated shape to permit easier passage through tissues disposed between the surgeon and the proximal surface 30 of the bone portion 10. For example, in another embodiment, the tissue guard 120 may be replaced with a simple cylindrical sleeve fitted into a conical piece at the distal end of the body of the instrument. The tapered conical shape of the tissue guard 120 shown in FIGS. 1, 2, 4 and 7, however, may be desirable for minimizing mechanical stress at the joints between the tissue guard 120 and body 140.

In an embodiment, the end of the body 140 nearest the tissue guard 120 has a threaded nipple (not shown in FIG. 1) of diameter larger than the diameter of the probe 160. In the instrument 100, the threaded nipple is integrally formed with the end of the body 140. In another embodiment, the threaded nipple may be secured to the distal end of the body 140 by a mechanical device or an adhesive. In all such embodiments, the tissue guard 120 is provided with a complementary threaded surface such that the tissue guard 120 and body 140 are secured by threading the tissue guard 120 onto the threaded nipple of the body 140. In such embodiments, the tissue guard 120 may be formed from injection molded plastic or from machined metal. In other embodiments, the tissue guard 120 may be formed as a single, seamless piece with the body 140.

The tissue guard 120 and probe 160 are concentrically arranged such that the distal end of the tissue guard 122 abuts the proximal surface 30 of the bone portion 10 in a manner similar to that of a bone plate or fastener head. Accordingly, the tissue guard 120 and indented hook 165 cooperate such that their relative position (and, therefore, distance) provides an accurate measurement of the depth of the hole 20 such that a screw or fastener may be selected whose length is accommodated by the hole 20.

In the embodiment of the invention provided by the instrument 100, movement of the sealed housing 130 is effective to shift the position of the probe 160 because the probe 160 and sealed housing 130 are attached as shown in FIG. 3. A portion of the bottom side of the sealed housing 130 is formed into a mating surface 132. The probe 160 is encircled by and secured within the portion of the bottom side of the sealed housing that forms the mating surface 132. In an embodiment, the probe 160 is interference press-fit into the bottom piece 139 of the sealed housing 130. Also shown in FIG. 3 are the mechanical parts of the sealed housing 130, including the top piece 138, bottom piece 139, and seal 136. In an embodiment, the seal 136 is an o-ring seal, which is robust to repeated contamination and sterilization. In addition, FIG. 3 shows the display window 150, which in an embodiment of the invention, is provided by a polycarbonate lens. The compartment 134 within the sealed housing 130 provides the mechanical support for the electronic sensor and display (not shown in FIG. 3). As described below, the electronics secured to the compartment 134 within the sealed housing 130 comprise the read-head assembly of an inductive or capacitive or other sensor, a display, and a power source (such as a battery).

In the embodiment of the sealed housing 130 shown in FIG. 3, electronic components (including an electronic sensor, display, and power source) are sealed inside the compartment 134 with an o-ring seal 136. In addition, the sealed housing 130 may be sealed with epoxy, glue, or other adhesives. In other embodiments, the sealed housing 130 may be mechanically sealed with hardware, such as screws or snaps within the compartment 134. Although the embodiment of the sealed housing 130 shown in FIG. 3 is designed to remain sealed both during surgery and sterilization, it will be appreciated by those skilled in the art that in an alternative embodiment, the sealed housing 130 may be designed to partially or completely disassemble for sterilization. All these features and variations are contemplated within the scope of the present invention.

When sealed, the embodiment of the sealed housing 130 shown in FIG. 3 is water resistant to several atmospheres of pressure. Moreover, the materials used to manufacture the sealed housing 130 are selected to be chemically inert to chemical contaminants or sterilization fluids, both at room temperature and at the temperatures required for sterilization in an autoclave. For example, the sealed housing 130 may be molded from acrylic, polyester, PVC, or other chemically inert plastic material. In other embodiments, the sealed housing may be made from metals, such as aluminum, brass, or stainless steel. The sealed housing 130 is also designed to provide only soft, rounded edges that are safe for use in a surgical environment. For example, the embodiment of the sealed housing 130 shown in FIGS. 1 through 5 is in substantial compliance with the Underwriters Laboratories sharpness test UL 1349.

Although the instrument 100 shown in the attached drawings includes a display, it will be understood by those of skill in the electronic arts that the present invention may be practiced using an external display in communication with a wireless device. In the instrument 100, a wireless transmitter may be connected to the read-head assembly within the sealed housing 130. In such wireless embodiments, a wireless receiver would be positioned a short distance away from the surgical depth gauge (for example, on a platform near the operating table), and an electronic display would be connected to the wireless receiver. In addition, as a supplement to a visual display, the instrument may be provided with an audio readout capability that may, for example, beep or provide another audible signal when the instrument senses that movement of the probe has stopped, and there has been an appropriate interval in which to take a measurement. In addition, the instrument may include the capability for the distance displayed to also be audibly conveyed through a simulated voice from a speaker maintained within the instrument. In this manner, the surgeon's determination of the distance may also be verified from the audible articulation of the distance, providing further confidence in the accuracy of the reading.

Figures 4, 5, 6A, 6B:
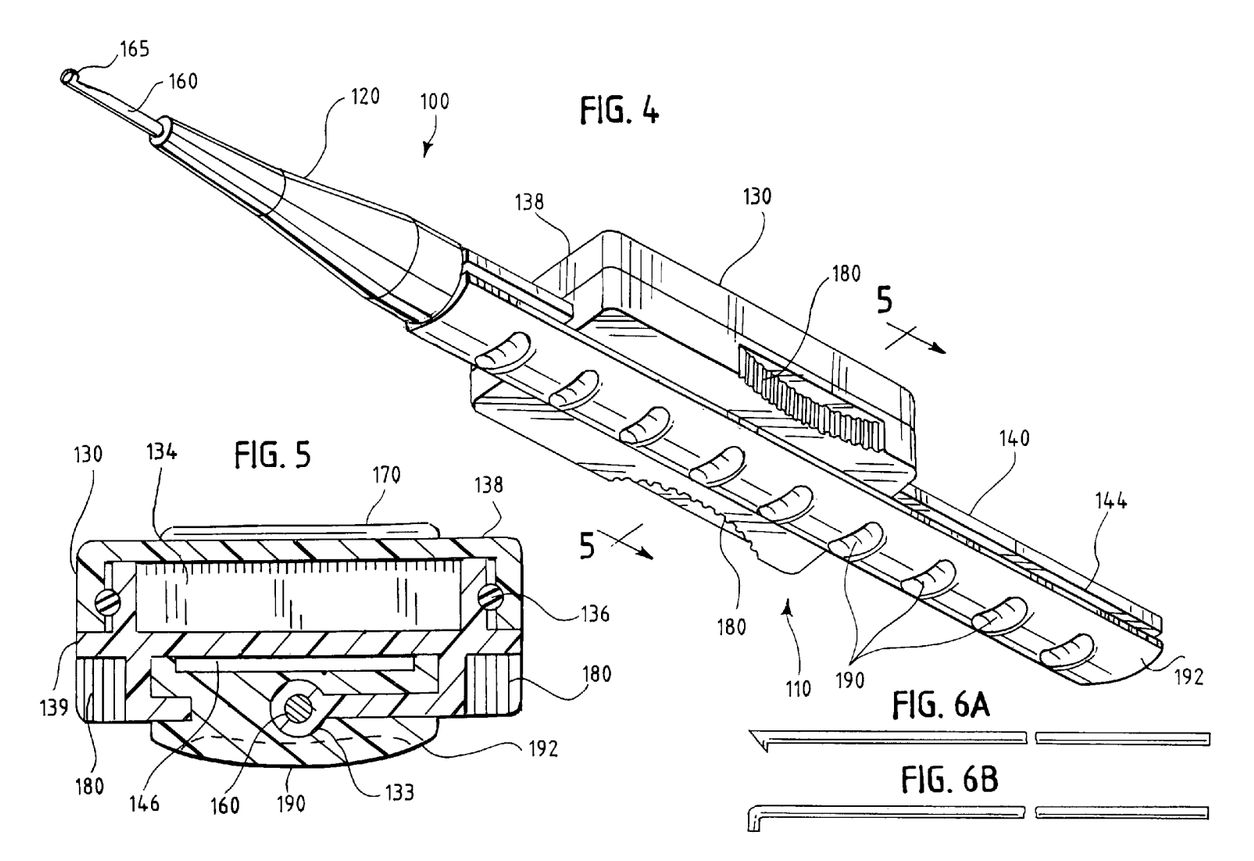
FIG. 4 shows a perspective view from below of a surgical depth instrument in accordance with an embodiment of the present invention.
FIG. 5 shows a cross-section view of the sealed housing and body of a surgical depth instrument in accordance with an embodiment of the present invention, taken at section line 5-5 of FIG. 4.
FIG. 6A shows a probe with a barb in accordance with an embodiment of the present invention.
FIG. 6B shows a probe with a hook in accordance with an embodiment of the present invention.

A perspective view of the instrument 100 from the bottom is shown in FIG. 4. As shown in FIG. 4, the present invention includes several ergonomic features in addition to the top ridges 170 (shown in FIGS. 1 and 3). In particular, the instrument 100 includes symmetrically shaped side grooves with ridges 180 and finger grooves 190. As shown in the cross-sectional end view of FIG. 5, the finger grooves 190 are formed in the convex bottom side 192 of the body 140. In accordance with an embodiment of the method of the present invention, a surgeon would place a forefinger on a first side groove 180, a thumb on the opposing side groove 180, and the rest of the fingers on the finger grooves 190 integrated with the body 140. The ergonomic design of the present invention permits a surgeon to use the system and perform the method of the present invention with a single hand, either right or left.

Moreover, the present invention leaves the bottom side 192 entirely unobstructed so that the surgeon is always free to grab the body 140.

Some structural features of the invention shown in FIG. 5 have the advantage of permitting the instrument 100 to be disassembled and reassembled for sterilization. In particular, the sealed housing 130 and body 140 are slidably connected along a mating surface 132 of the sealed housing 130 and a reciprocal mating surface 142 formed within the side groove 144 of the body 140. The probe 160, which is engaged in the sealed housing 130, slides through the side grooves 144 of the body 140 and into a funneled cylindrical channel formed in the tissue guard 120. In another embodiment, the tissue guard 120 may provide a keyhole-shaped (rather than a cylindrical) channel to permit probe tips without cylindrical symmetry (i.e., tips such as the barb 167 or hook 169 shown in FIGS. 6A and 6B) to pass through during disassembly and reassembly of the instrument 100. Moreover, in such other embodiments, the tissue guard 120 may be rotated after assembly to prevent the distal end of the probe 160 from retracting within the tissue guard 120. Such a rotation is permitted when the tissue guard 120 threads onto the body 140, as described above. Without a keyhole-shaped channel, probe tips of non-cylindrical symmetry must have a maximum width less than the total diameter of the cylindrical channel in the tissue guard 120.

When slidably connected as shown in the instrument 100, the present invention does not require oil lubricants, such that the materials are entirely compatible with a surgical environment. Referring to FIG. 3, the instrument 100 is shown in cross-section (along the plane 4-4 through the sealed housing 130 shown in FIG. 3) viewed facing the distal end. The sealed housing 130 is shown in FIG. 3, with the compartment 134 (again, shown without internal electronic components), and top ridges 170. The seal 136 is also shown disposed between the top piece 138 and bottom piece 139 of the sealed housing 130. In addition, the mating surface 132 of the bottom piece 139 is shown engaged with the reciprocal mating surface 142 formed by and within the side groove 144 of the body 140. Also, the probe 160 is shown concentric to the end of the mating surface 132 of the bottom piece 139. By permitting a slidable connection between the sealed housing 130 and body 140, the mating surface 132 of the housing 130 and complementary mating surface of the body facilitate disassembly and reassembly of the instrument 100 for sterilization. Moreover, because the surfaces are not symmetric from left to right along the line 5-5 in FIG. 5, the system can be reassembled only with the display facing the distal end. The non-symmetrical design of the complementary mating surfaces thus prevents the present invention from being reassembled incorrectly.

The electronic sensors used in the system and method of the present invention comprise capacitive and inductive sensors and sensor assemblies. Sensors and sensor assemblies are readily available commercially from manufacturers such as Sylvac and Mitutoyo. For example, capacitive and inductive read-head and write-head assemblies are used in digital calipers, such as that made by Mitutoyo America Corporation, 965 Corporate Blvd., Aurora, Ill., and by Guilin Measuring and Cutting Works, 106 Chongxin Road, Guangxi, Guilin 541002, Peoples Republic of China. In general, the electronic sensor secured within the compartment 134 of the sealed housing 130 takes the form of a conventional electronic sensor, display, and power source assembly for use in a length measuring device relying on inductive or capacitive or other elements. For some embodiments, inductive elements may provide advantages to the extent that inductors provide more uniform and consistent measurements through a wider variety of environmental conditions. For example, the instrument 100 may be built with a pattern of inductive loops laid down along the sensor pattern compartment 146 of the body 140, and a facing read-head assembly secured within the compartment 134 of the sealed housing 130.

In various embodiments of the present invention, the electronic sensor may be connected with a microprocessor or other digital electronic device in order to produce an output for an electronic display, such as a liquid crystal display or light-emitting diode display. In other embodiments, the microprocessor or other digital electronic device may be connected to a wireless transmitter, as described above. In some embodiments, a signal conditioning circuit may interpose the inductive or capacitive elements of the electronic sensor and the microprocessor or other digital electronic device used to drive the display, thus ensuring that correct input current and voltage levels are provided to the various components. As will be recognized by skilled artisans, a power source, such as a primary or secondary battery, may be connected to the signal conditioning circuit or to the microprocessor directly.

The microprocessor or other digital electronic device used to drive the display may be configured to provide depth measurements in inches, millimeters, or fractions thereof. In various embodiments, the sealed housing 130 may include buttons that permit the surgeon to select how the preferred unit of measurement is displayed. In an embodiment, the microprocessor or other digital electronic device is configured to provide a positive reading for depth as the probe 160 is extended from the proximal surface 30 toward the distal surface 40 of the bone portion 10, and a zero reading when the probe 160 is retracted so that the catch of the hook is flush with the distal end of the tissue guard. In another embodiment, the present invention may be configured to permit a re-zeroing of the device by providing a calibration button. In still other embodiments, the present invention may provide on and off buttons (or an on/off toggling button), or a button for storing and holding the measurement presently shown on the display for reading after the probe 160 has been moved. In such embodiments, the buttons may be formed in the sealed housing 130.

The electronic display of the present invention is selected for quick and easy visual inspection during surgery. The electronic display, however, may provide information in addition to depth measurements. For instance, the present invention may be provided as part of a kit (not shown) including a bone plate that mates with a head and shank formed on a screw. The electronic sensor may be calibrated to compensate for or provide an offset corresponding to a portion of the screw head and shank received within the bone plate. Accordingly, the present invention could be configured to suggest a particular screw selected from the kit for use with the bone plate, rather than a measurement of length. The electronic display may also provide an indication that the reading is not stable, for example, because the tissue guard 120 and probe 160 are not generally stationary relative to one another. This event is more typical when compressible soft tissue is caught on the indented hook 165, or between the tissue guard 120 and the proximal surface 30, or in general when the distal end of the probe 160 is not securely positioned. In this respect, it should be noted that the probe 160 may be provided without any mechanical securement at its distal end. As an example, the distal end of the probe 160 may be inserted to a depth such that its distal end is coincident with, but generally does not extend beyond, the distal edge 26 of the hole 20. In using such an embodiment, the surgeon may place a stop or finger on the distal surface 40 of the bone portion 10 to stop the probe 160 when it has reached the distal edge 26.

In an embodiment, the electronic sensor and accompanying electronics can be shielded from electromagnetic interference, for example, by coating the inside of the sealed housing 130 with a conductive paint containing metal microspheres. Such shielding may be effective in reducing interference from low frequency magnetic fields, or other stray electromagnetic fields. Shielding is desirable at least because the method of the present invention may be practiced in conjunction with the use of a magnetic pad for holding surgical instruments (not shown in FIGS. 1-3).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

A variety of embodiments of the invention are described and illustrated herein; variations of those embodiments will become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. It is not the intent of the inventors to surrender or otherwise dedicate any valid claim to the subject matter described herein to the public, and the following claims are intended to capture the entire scope of the invention herein described.

What is claimed is:

1. A generally elongated instrument for measuring the depth of a hole with a first edge and a second edge, the instrument having a longitudinal axis, the instrument comprising:
    a first generally elongated member substantially oriented along the longitudinal axis and which is insertable in the hole, the first member comprising a portion positionable against a first surface in which the first edge of the hole is formed;
    a second generally elongated member substantially oriented along the longitudinal axis and which is slidably connected to the first member, the second member comprising a portion positionable against a second surface in which the second edge of the hole is formed and a sensor that generates an electronic signal that varies in relation to the distance between the first member and the second member; and
    an electronic display substantially oriented along and generally centered about the longitudinal axis for displaying information representative of the distance measured by the sensor.

2. The instrument of claim 1 wherein the portion of the first member positionable against the first surface is selected from the group consisting of a barb, a hook, an indented hook, an optical sensor, and an ultrasonic transducer.

3. The instrument of claim 1 wherein the sensor of the second member comprises a capacitor.

4. The instrument of claim 1 wherein the sensor of the second member comprises an inductor.

5. The instrument of claim 1 wherein the electronic display is selected from the group consisting of a liquid crystal display and an LED display.

6. The instrument of claim 1 wherein the sensor of the second member is contained within a sealed housing.

7. The instrument of claim 6 wherein the sealed housing comprises at least two sides shaped substantially symmetrically to accommodate both left-handed and right-handed use.

8. The instrument of claim 1 wherein the first member further comprises a mating surface and the second member further comprises a complementary mating surface slidably engaged with the mating surface of the first member.

9. The instrument of claim 1 wherein the first member and the second member are slidably detachable to facilitate sterilization.

10. The instrument of claim 1 wherein the portion of the second member positionable against the second surface comprises a tissue guard.

11. The instrument of claim 1 wherein the instrument comprises a substantially cylindrical form factor.

12. The instrument of claim 1 wherein the sensor is connected to a wireless transmitter.

13. A generally elongated instrument for measuring the depth of a hole with a first edge and a second edge, the instrument having a longitudinal axis, the instrument comprising:
    a first generally elongated member substantially oriented along the longitudinal axis and which is insertable in the hole, the first member comprising a portion positionable against a first surface in which the first edge of the hole is formed; and
    a second generally elongated member substantially oriented along the longitudinal axis and which is movably connected to the first member, the second member comprising:
        a portion positionable against a second surface in which the second edge of the hole is formed;
        a sensor that generates an electronic signal that varies in relation to the distance between the first member and the second member;
        an electronic display substantially oriented along and generally centered about the longitudinal axis and in communication with the sensor that displays information relating to the distance measured by the sensor; and
    wherein the first member and the second member are movably connected along a first surface of the first member and a second surface of the second member.

14. The instrument of claim 13 wherein the portion of the first member positionable against the first surface is selected from the group consisting of a barb, a hook, an indented hook, an optical sensor, and an ultrasonic transducer.

15. The instrument of claim 13 wherein the sensor of the second member comprises a capacitor.

16. The instrument of claim 13 wherein the sensor of the second member comprises an inductor.

17. The instrument of claim 13 wherein the electronic display is a display selected from the group consisting of a liquid crystal display and an LED display.

18. The instrument of claim 13 wherein the sensor of the second member is contained within a sealed housing.

19. The instrument of claim 18 wherein the sealed housing comprises at least two sides shaped substantially symmetrically to accommodate both left-handed and right-handed use.

20. The instrument of claim 13 wherein the first member and the second member are detachable to facilitate sterilization.

21. The instrument of claim 13 wherein the portion of the second member positionable against the second surface comprises a tissue guard.

22. The instrument of claim 13 wherein the electronic display is in communication with the sensor using a wireless transmitter and a wireless receiver.

23. The instrument of claim 22 wherein the reciprocating means comprises a sensor and a sealed housing, the sensor being contained within the sealed housing.

24. The instrument of claim 23 wherein the sealed housing has at least two sides shaped substantially symmetrically to accommodate both left-handed and right-handed use.

25. The instrument of claim 13 wherein the instrument comprises a substantially cylindrical form factor.

26. A generally elongated instrument for measuring the depth of a hole with a first edge and a second edge, the instrument having a longitudinal axis, the instrument comprising:
   an insertable means for positioning against a first surface in which the first edge of the hole is formed;
   a reciprocating means for positioning against a second surface in which the second edge of the hole is formed, the insertable means and the reciprocating means being movably connected and concentrically arranged with each other along the longitudinal axis;
   a measuring means for electronically determining the distance between the first surface and the second surface; and
   a display means substantially oriented along and generally centered about the longitudinal axis for displaying information representative of the distance determined by the measuring means.

27. The instrument of claim 26 wherein the insertable means comprises a portion selected from the group consisting of a barb, a hook, an indented hook, an optical sensor, and an ultrasonic transducer.

28. The instrument of claim 26 further comprising a display means for displaying information relating to the distance between the first surface and the second surface.

29. The instrument of claim 28 wherein the display means is a display selected from the group consisting of a liquid crystal display and an LED display.

30. The instrument of claim 26 wherein the measuring means comprises a wireless transmitter.

31. The instrument of claim 26 wherein the measuring means comprises a capacitor.

32. The instrument of claim 26 wherein the measuring means comprises an inductor.

33. The instrument of claim 26 wherein the insertable means comprises a mating surface and the reciprocating means comprises a complementary mating surface, and wherein the insertable means and the reciprocal means are slidably connected along the mating surface and the reciprocal mating surface.

34. The instrument of claim 26 wherein the insertable means and the reciprocating means are detachable to facilitate sterilization.

35. The instrument of claim 26 wherein the reciprocating means comprises a tissue guard positionable against the second surface.

36. The instrument of claim 26 wherein the instrument comprises a substantially cylindrical form factor.

37. The instrument of claim 26 wherein the display means is an electronic display.

38. The instrument of claim 37 wherein the electronic display is selected from the group consisting of a liquid crystal display and an LED display.

* * * * *